(12) United States Patent
McCormick et al.

(10) Patent No.: US 6,617,496 B1
(45) Date of Patent: Sep. 9, 2003

(54) EFFECTING VIRUS RESISTANCE IN PLANTS THROUGH THE USE OF NEGATIVE STRAND RNAS

(75) Inventors: Francis P. McCormick, Albany, CA (US); Kenneth A. Barton, Middleton, WI (US); William F. Swain, Madison, WI (US)

(73) Assignee: Monsanto Company, St. Louis, MO (US)

( * ) Notice: Subject to any disclaimer, the term of this patent is extended or adjusted under 35 U.S.C. 154(b) by 0 days.

(21) Appl. No.: 06/788,002

(22) Filed: Oct. 16, 1985

(51) Int. Cl.$^7$ .................. C12N 15/33; C12N 15/82; C12N 15/84; A01H 5/00; A01H 5/10

(52) U.S. Cl. ................ 800/286; 800/280; 800/294; 800/301; 800/317.3; 435/418; 435/419; 435/468; 435/469; 536/23.72; 536/24.5

(58) Field of Search .................. 435/68, 172.3, 435/317, 320, 252.2, 69.1, 320.1, 418, 419, 468, 469; 800/1, 205, 250, 255, DIG. 43, 280, 286, 294, 301, 317.3; 536/27, 23.72, 24.5; 935/29, 56, 67, 72

(56) References Cited

U.S. PATENT DOCUMENTS 5,580,716 A * 12/1996 Johnston et al. ............ 435/5

FOREIGN PATENT DOCUMENTS

EP         84112647     8/1985     ........... 435/172.3

OTHER PUBLICATIONS

Goodman et al. 1987. Science 236:48–54.*
Mehsi et al. 1982. Virology 118:64–75.*
Palukaitis et al. 1984. pp. 420–429 In: Plant–microbe Interact. vol. 1, Kosuge et al., eds., Macmillan. New York.*
Izant et al. 1984. Cell 36:100 7–1015.*
Chang et al. 1985. Mol. Cell. Biol. 5(9):2341–2348.*
Barton et al. 1983. Cell 32:1033–1043.*
Coleman et al. 1984. Cell 37:429–436.*
Eckhardt, et al., "Blocking of the Initiation of Protein Biosynthesis by a Pentanucleotide Complementary to the 3'End of Escherichia Coli 16 SrNA," *The Journal of Biological Chemistry*, vol. 254, pp. 11185–11188 (Nov. 25, 1979).
Izant, et al., "Inhibition of thymidine Kinase Gene Expression by Anti–Sense RNA: A molecular Approach to Genetic Analysis," *Cell*, vol. 36, pp. 1007–1015 (Apr. 1984).
Jayaraman, et al., "Selective inhibition of *Escherichia coli* protein synthesis and growth by nonionic oligonucleotides complementary to the 3'end of 16S rRNA," *Proc. Natl. Acad. Sci. USA*, vol. 78, pp. 1537–1541 (Mar. 1981).

Marx, "New Ways to 'Mutate 'Genes," *Research News*, vol. 24, p. 819 (Aug. 1984).
Mizuno, et al., "A unique mechanism regulating gene expression: Translational inhibition by a complementary RNA trascript (micRNA)," *Proc. Natl. Acad. Sci. USA*, vol. 81, pp. 1966–1970 (Apr. 1984).
Stephenson, etal., Inhibition of Rous sarcoma viral RNA translation by a specific oligodeoxyribonucleotide, *Proc. Natl. Acad. Sci. USA*, vol. 75, pp. 285–288 (Jan. 1978).
Taniguchi, et al., "Inhibition of QB RNA 705 ribosome initiation complex formation by an oligonucleotide complementary to the 3'terminal region of *E. coli* 16S ribosomal RNA," *Nature*, vol. 26, pp. 770–772 (Oct. 26, 1978).
Travers, "Regulation by anti–sense RNA," *Nature*, vol. 311, p. 410 (Oct. 4, 1984).
Zamecnik, et al., "Inhibition of Rous sarcoma virus replication and cell transformation by a specific oligodeoxynucleotide," *Proc. Natl. Sci. USA*, vol. 75, pp. 280–284 (Jan. 1978).
Calvet, et al., "Base–Pairing Interactions between Small Nuclear RNAs and Nuclear RNA Precursors as Revealed by Psoralen Cross–Linking in Vivo," *Cell*, vol. 26, pp. 363–370 (Nov. 1981).
Lerner, et al., "Are snRNPs involved in splicing?" Nature, vol. 283, pp. 220–224 (Jan. 10, 1980).
Mount, et al., "The U1 Small Nuclear RNA–Protein Complex Selectively Binds a 5'Splice Site In Vitro," *Cell*, vol. 33, pp. 509–518 (Jun. 1983).
Murray, et al., "Mechanism for RNA splicing of Gene Transcripts," Febs Letters, vol. 106, pp. 5–7 (Oct. 1979).
Pederson, et al., "Nuclear RNA–Protein Interactions and Messenger RNA Processing," *The Journal of Cell Biology*, vol. 97, pp. 1321–1326 (Nov. 1983).
Rogers, et al., "A mechanism for RNA splicing," *Proc. Natl. Acad. Sci. USA*, vol. 77, pp. 1877–1879 (Apr. 1980).
Letter from Dr. Leonard E. A. Godfrey to Dr. Goldberg Re: Invention No. R252, "Regulation of Gene Expression by Employing Translational Inhibitin by a Complementary RNA Transcript," and InventionvNo. R262, "The use of mRNA Interfering Complementary RNAs (micRNAs) to Specifically Regulate the Expression of Individual Bacterial Genes," and enclosed documents.

\* cited by examiner

*Primary Examiner*—David T. Fox
(74) *Attorney, Agent, or Firm*—Quarles & Brady LLP

(57) ABSTRACT

A strategy for effecting virus resistance in plants causes the transcription in the plant cells of negative RNA strands which are substantially complementary to a target RNA strand. The target RNA strand can be an mRNA transcript created in gene expression, a viral RNA, or other RNA present in the plant cells. The negative RNA strand is complementary to at least a portion of the target RNA strand to inhibit its activity in vivo.

22 Claims, 5 Drawing Sheets

US 6,617,496 B1

EFFECTING VIRUS RESISTANCE IN PLANTS THROUGH THE USE OF NEGATIVE STRAND RNAS

TECHNICAL FIELD

The present invention relates to the field of the application of recombinant DNA technology to the genetic transformation, or genetic engineering, of higher plants. More specifically, the invention relates to a strategy for effecting somatic changes in higher plants through the use of negative RNA strands, so as to control gene expression in plants or to achieve other useful somatic effects, such as disease resistance.

DESCRIPTION OF THE PRIOR ART

It has now become possible to construct fragments, of genetic material, i.e. DNA, in vitro, and to transform those fragments into plasmids contained in bacteria. It has also become possible to use cloned fragments, or to clone entire genes, in bacterial plasmids known as vectors, which can carry those fragments, or genes into other cells. Suitable vectors have been developed which can be used to genetically transform individual plant cells from which full intact, plants can be regenerated. It is has been documented that foreign genes can be stably inserted into the genome of plant cells, and that whole, intact, somatically normal and reproductively competent plants can be reconstructed therefrom. K. A. Barton, et al., *Regeneration of Intact Tobacco Plants Containing Full-Length Copies of Genetically Engineered T-DNA, and Transmission of T-DNA to R1 Progeny*, 32 Cell 1033 (April 1983). Investigators have reported that they have been able to introduce complete foreign genes into plant cells, and obtain gene expression in those plant cells, with the understanding and expectation that the cells are capable of being regenerated into whole, intact, plants. European patent application S.N. 84302582.2, filed Apr. 16, 1984 (Kemp); PCT application number WO84/02920 and WO84/02913, both filed Jan. 16, 1984 (Fraley). In general, inserted genes will function in plants only when constructed as chimeric insertions with proper plant gene control regions appropriate for plant systems.

Most of the current strategies used for creating genetically engineered plants involve modification on a cellular level of plant cells through the use of the natural plant transforming agent *Agrobacterium tumefaciens*, which has the natural ability to infect dicotyledonous plants and to transfer a certain portion of the DNA (referred to as T-DNA) of the *A. tumefaciens* into the plant cell. Other techniques have been proposed, not involving *A. tumefaciens*, for transforming individual plant cells, particularly protoplasts, of both dicots and monocots. The principle obstacle to successful genetic engineering of a wide number of plant species at present is the difficulty in regenerating many plant species from callus culture or protoplasts. For those species for which regeneration techniques are currently available, genetic transformation of cells in culture can result in full foreign gene expression in intact otherwise normal plants. For plant species for which regeneration techniques are not presently refined, once those techniques are developed, regular genetic transformation of intact plants of those plant species will become a common practice.

Once it is possible to genetically engineer a plant species, the question then becomes what logical genetic transformations can be achieved in the plant in order to make the plant more suitable for the agricultural or horticultural uses for which it is normally intended. One common strategy for the utilization of genetic engineering in plants is to introduce exogenous protein genes into plants to cause expression in the plant of a protein which may be useful for one or more purposes, such as disease resistant, insect resistance, enzymatic activity, utility as a food ingredient, etc.

The invention described here provides an alternative strategy for the use of genetic engineering techology in plants to achieve useful somatic changes to plants, not involving the expression of any exogenous proteins, but instead controlling the expression of an endogenous protein or the operation of a protein gene or other DNA or RNA factor naturally introduced into the plant cells through outside agents, such as agents of disease or infection.

It has been previously recognized that artificially constructed negative strand RNAs will hybridize with complementary RNAs in vivo. This phenomenon has been utilized to investigate the regulatory mechanisms of gene expression in *E. coli*. Mizuno et al, *Regulation of Gene Expression by a Small RNA Transcript (mic RNA) in Escherichia coli K-12*, 10 Proc. Japan Acad. 59, Ser. B, pp. 335–338 (1983), Mizuno et al, *A Unique Mechanism Regulating Gene Expression: Translational Inhibition by a Complementary RNA Transcript (mic RNA)*, 81 Proc. Natl. Acad. Sci. USA, pp. 1966–1970 (1984).

SUMMARY OF THE INVENTION

The present invention relates to a method for performing useful genetic transformations of plants to achieve useful somatic changes in the plants themselves, not specifically involving the expression of exogenous proteins. The method involves the introduction into the plant genome of DNA sequences constructed for the transcription of negative strand RNA which is substantially complementary to target endogenous or naturally introduced RNA strands, whose function it is desired to inhibit so as to prevent either the expression of an endogenous protein gene or the operation of a naturally introduced RNA or DNA, such as occurs through certain types of parasitic or disease infection.

It is an object of the present invention to provide a strategy for genetically engineering plants to create plants having useful somatic characteristics without necessarily causing the expression of exogenous proteins.

It is another object of the present invention to provide a method for controlling endogenous gene expression in plants in general.

Other objects and advantages of the present invention will become apparent from the following specification.

GENERAL DESCRIPTION AND PREFERRED EMBODIMENTS OF THE PRESENT INVENTION

Figure 1:
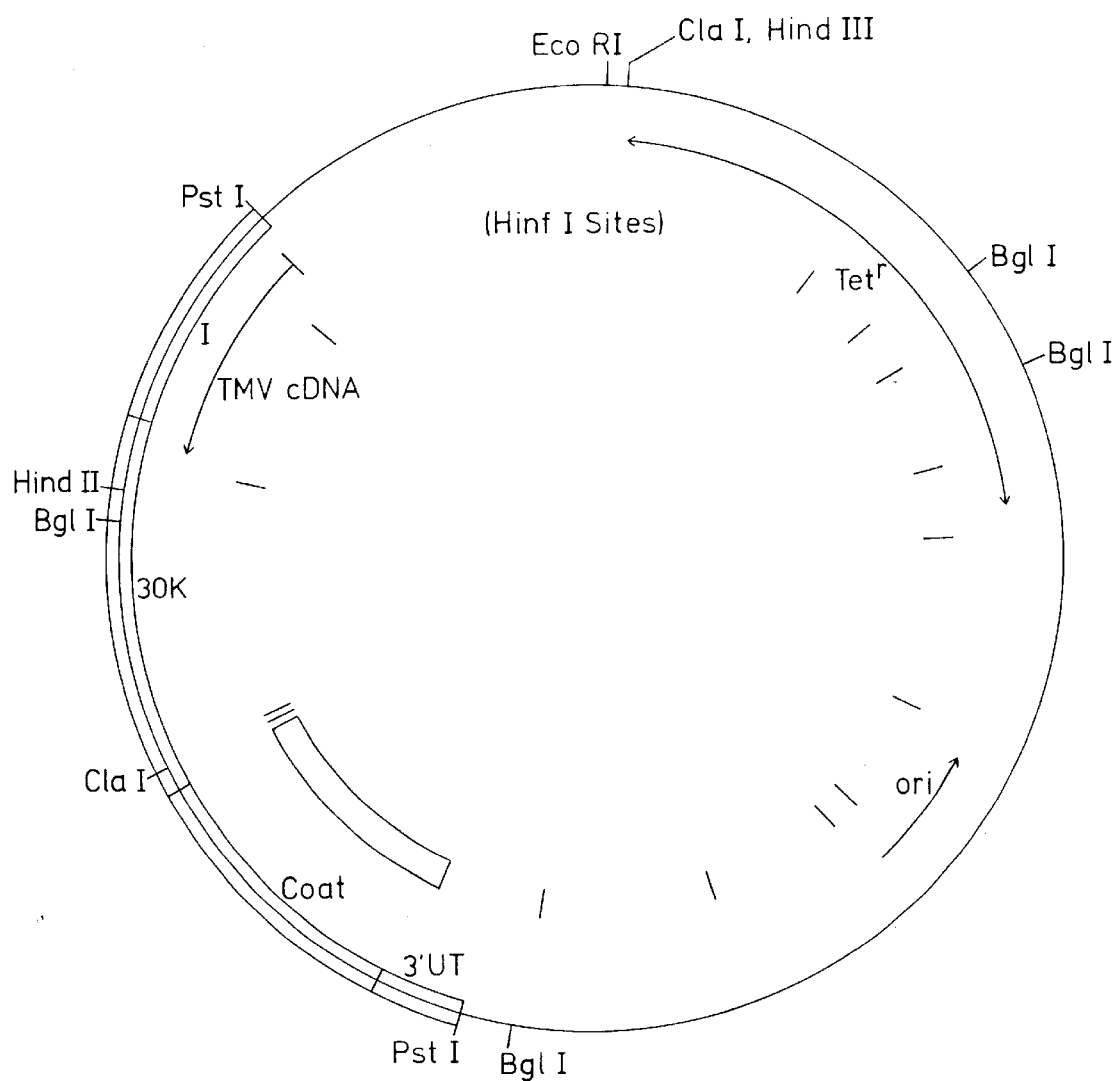
FIG. 1 is a schematic diagram showing the restriction enzyme map for plasmid pOM5H2. a starting material in one of the examples of the present invention.
Figure 2:
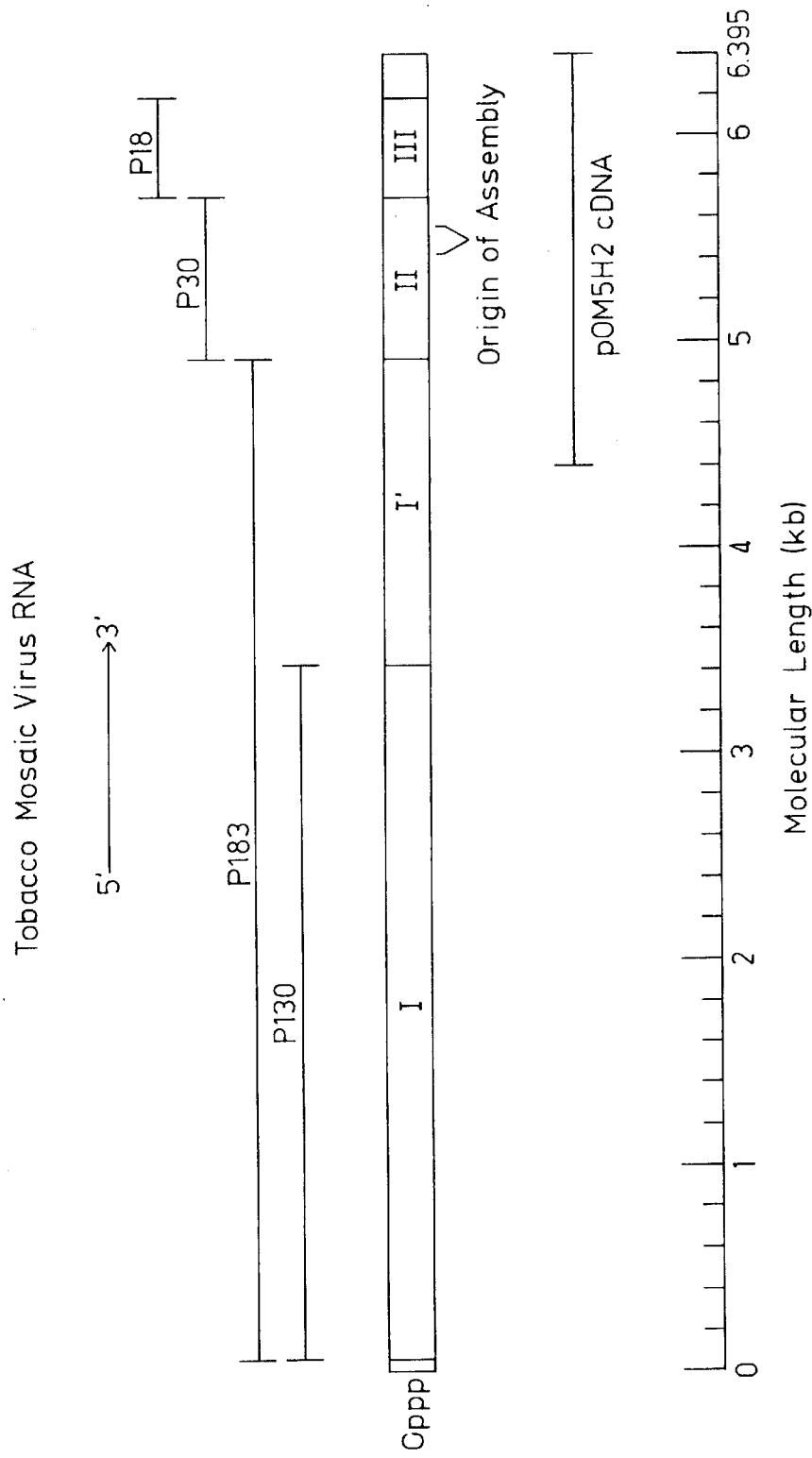
FIG. 2 is a schematic diagram of the tobacco mosaic virus RNA.
Figure 3:
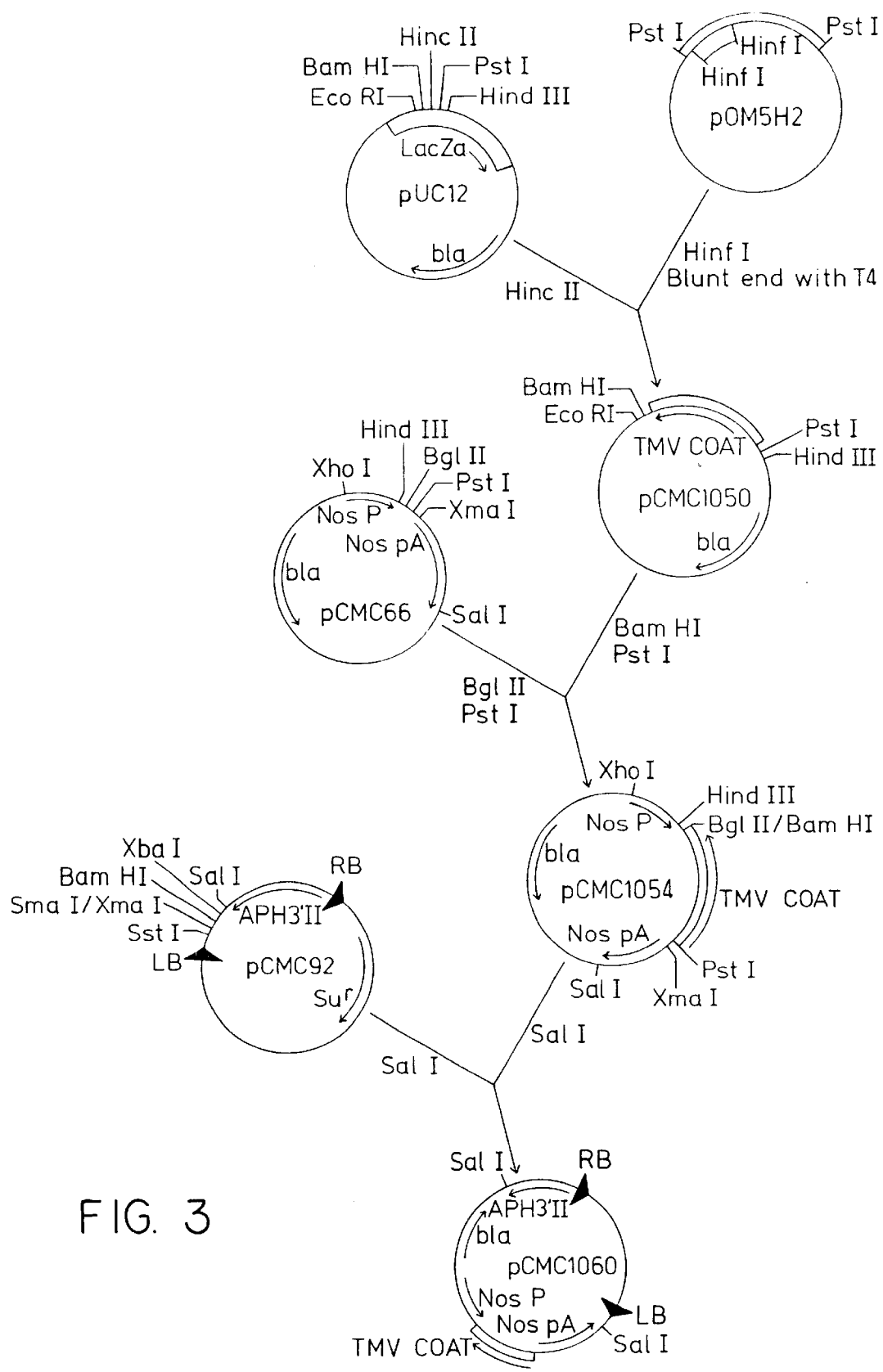
FIG. 3 is a schematic diagram showing the plasmid manipulations according to a method detailed in Example 1 below.

In summary, the present invention describes a generalized strategy to effect somatic changes in higher plants by the use of DNA sequences inserted into the genome of the plants to cause the transcription of specific negative RNA strands which will hybridize with selected target RNA strands to selectively inhibit the translation, reverse transcription, or other operation on, or function of, the target RNA sequence. The hybridization of the negative RNA strand to the target RNA can be used directly to control (i.e. inhibit) expression of an endogenous gene, if the target RNA strand is an mRNA transcript of a normally expressed gene in a plant cell. This invention can also be used to inhibit certain disease processes, such as the reverse transcription, translation, or replication of an RNA virus sequence. It may also prove useful as a gene regulator to hybridize with RNA strands which may otherwise react with promoters or suppressors in RNA processing, or other regulators, to control gene expression.

In normal nuclear conditions in vivo, DNA is double stranded, and transcription of the DNA, to create RNA, is generally asymmetrical. The asymmetry is that the transcription promoter is oriented relative to one end of a DNA coding sequence such that one, and only one, strand of the DNA is transcribed. The RNA produced by such normal transcription is presumably useful to the organism and is designated positive strand RNA. The RNA sequence which is the base-pair complement of a positive strand RNA is referred to as negative strand RNA. The negative strand RNA can be produced by transcription of the opposite DNA strand relative to that which is normally transcribed. Because of the asymmetry of promoter transcription initiation, transcription of the opposite DNA strand does not naturally occur. Negative strand RNA creation thus involves the creation of chimeric genes having transcription regulating signals on a double stranded DNA sequence in the opposite or reverse orientation from that which normally produces the positive strand RNA.

A negative strand RNA, as the term is used herein, refers to a specific RNA strand, coded by specially constructed DNA sequence, which has substantial complementarity to a target RNA strand previously selected. The complementary portion of the negative RNA strand must be sufficient in length and sufficiently complementary to the target RNA sequence so that sequence recognition will occur under normal cytoplasmic conditions with the target RNA sequence selected. The sequence recognition will normally occur in the form of hybridization of the positive and negative strand RNAs to inactivate the positive strand RNA but may also include other RNA to RNA interactions which serve to interfere with positive strand RNA activity.

As used herein, a negative RNA DNA sequence is a chimeric DNA sequence specifically constructed and adapted to be used in a plant transcription vector to transform a plant to cause the plant to transcribe a pre-selected negative RNA strand. The negative RNA DNA sequence will require a promoter to initiate negative RNA sequence transcription. The transcription itself will be normal although on the opposite DNA strand from usual. The negative RNA DNA sequence may or may not include polyadenylation or ribosome-binding sequences. If it is desired that the reverse RNA sequences be constitutive in the cytosol of the plant cells, then polyadenylation or some other form of 3' end processing or termination signal may be appropriate.

The target RNA as used in the present invent-ion refers to an endogenous or naturally occurring RNA sequences. Endogenous sequences would typically be mRNA sequences created during the process of expression of an endogenous or engineered gene contained in the plant genome. Other endogenous RNA sequences include snRNAs, scRNAs, rRNAs, tRNAs, etc. Other naturally occurring target RNA sequences, as the term is used herein, are RNA sequences introduced into the plant cell by natural biological processes, such as parasitism or disease. Examples include the RNA of viruses and RNAs created by DNA of bacterial origin.

Examples of the practice of the present invention detailed herein relate specifically to tobacco plants and expression vectors operable in dicots. Tobacco was chosen as a model system for these examples primarily because of the present capability to regenerate tobacco plants from transformed individual tobacco cells, in a manner now known in the art. The expression vectors utilized herein are demonstrably capable of operation in cells of many dicotyledonous plants both in tissue culture and in whole plants. The invention disclosed herein is thus operable in dicotyledonous species to transform individual plant cells and to achieve full, intact plants in dicot plant species which can be regenerated from transformed plant calli. For those species not presently regenerable, the present invention is fully operable when the techniques for such regeneration become developed. In addition, chimeric expression vectors are also known and have been described in the literature which have been demonstrated to be operable in cells of some monocots, in particular in maize or corn at least in tissue culture. It is thus reasonable to expect that these vectors will also be operable in whole monocot plants when the techniques for regenerating these, plants are developed. The present invention is thus applicable to monocots as well as to dicots. It is intended within the scope of the present invention that the negative RNA strand activity is intended to effect a somatic change in the regenerated whole plant and its progeny. This somatic change may be morphological, such as when the expression of an endogenous gene is inhibited, or may be a somatic change only exhibited during a challenge to the plant, such as disease, drought, or other stress resistance.

The present invention may be better understood by reference to the following examples, which are intended to be exemplary and not limiting.

EXAMPLE 1

Disease Resistance Tobacco Mosaic Virus RNA

This example is directed toward the inhibition of the cellular disease process triggered by invasion of the tobacco mosaic virus. Tobacco mosaic virus (TMV) is a plant positive strand RNA virus whose RNA is translated and replicated as part of the disease process in the infected cell. The positive strand RNA of TMV is injected into the cytosol of an infected plant cell. Two genes on the positive strand RNA are then translated to produce two protein products which trigger, in turn, the production of a negative strand complement of the TMV RNA. The complement strand serves as a template for positive stand replication while two more subgenomic positive strand RNAs are translated into other proteins, one of which is the coat protein. The replicated positive strand RNAs are packaged by the coat proteins to make new TMV.

The strategy of this example is to transform plant cells so that they will constitutively transcribe negative RNA strands which will hybridize with the target RNA strand, and in this case the target RNA strand is the TMV RNA itself (the positive strand). To effectively neutralize the target TMV RNA by hybridizing to it so it is either not replicated by TMV host functions or not translated by the host functions.

In this fashion it is proposed to enhance plant resistance to tobacco mosaic virus infection, and to validate a model for inducing similar resistance in plants, to virus infection or to any pathogenesis which involves functioning of a pathogen nucleic acid in a host plant cell.

A plasmid has been described which contains a cDNA sequence which is the reverse transcript of a large part of the RNA of the tobacco mosaic virus. This plasmid is known as pOM5H2 (Meshi et al. *Virology,* 118: 64–65 (1982)). A restriction enzyme mapping of the pOM5H2 plasmid is illustrated in FIG. 1. The relationship of the pOM5H2 cDNA sequence to the entire TMV RNA is illustrated in FIG. 2. The cDNA segment is approximately 2 kilobases long and contains approximately ⅓ of the entire viral sequence, beginning from the 3' end. The cDNA sequence includes the 3' non-coding region, which has been reported for other distinct but similar viruses to have specific, unique structural features essential to viral replication in the infected cell (Ahlquist et al., *Plant Mol. Biol.* 3: 37–44 (1984)). From the location of the restriction sites in the plasmid pOM5H2, which can be determined from the method of construction of the plasmid, and from the sequence of TMV derived from other cDNA clones of TMV sequences, it is apparent that digestion with the restriction endonuclease Pst I yields the entire cDNA insert, which can thus be excised intact from the plasmid. Alternatively, digestion of the plasmid with the restriction enzyme Hinf I yields several fragments. One of the fragments from Hinf I digestion, designated Hinf IB (shown in FIG. 1), represents nucleotide position 5698 to 6365 of the sequence of the tobacco mosaic virus genome, and contains the coat protein coding region, 11 nucleotides at the 5' end of the sequence which are non-coding and a significant portion (174 of 203 base pairs) of the non-coding replication sequence at the 3' end of the coding region. Thus from the vector pOM5H2 two alternative techniques were used to obtain negative RNA strands which are useful in inhibiting the successful invasion of a host plant cell by an invading TMV virus. One technique was to cause construction of a negative transcript of the Pst I fragment, which would thus be a 2kb negative strand which could hybridize to the 3' most one-third of the viral RNA in the cell. The other technique was to use the Hinf IB fragment to cause construction of a negative transcript of the coat protein coding region to hybridize to the coat protein portion of the viral RNA or to the coat protein mRNA during protein synthesis. Both techniques were followed.

Coat Protein Negative RNA Strand

The Hinf IB fragment created by Hinf I digestion of pOM5H2 was separated from the Hinf I digest by electrophoresis. The fragment was then treated with T4 DNA polymerase to generate a blunt-ended fragment. The resulting blunt-end fragment was then blunt-end ligated with plasmid pUC12, which had been previously digested with Hinc II. The product of this blunt-end ligation is a plasmid pCMC1050 which contained the pOM5H2 Hinf IB fragment flanked by several unique restriction sites. The general scheme of this process is illustrated in FIG. 3.

The recombinant plasmid pCMC1050 was then digested with restriction enzymes Pst I and Bam HI to generate two fragments, the smaller of which was then selected and isolated for ligation with pCMC66. Plasmid pCMC66 is an intermediate expression vector having the promoter sequence and the polyadenylation sequence from the nopaline synthase gene from *A. tumefaciens*, which is operative in plants, inserted into a vector having useful unique restriction sites located adjacent to the promoter and the polyadenylation sequence. The vector pCMC66 had been previously digested with Pst I and Bg1 II. The ligation resulted in a plasmid, designated pCMC1054, which carries the TMV Hinf IB fragment in an inverse orientation with respect to the reading direction of the nopaline synthase promoter and polyadenylation sequences. The orientation of the Hinf IB fragment in pCMC1054 is dictated by the restriction site ends left on the fragment which will allow ligation into the digested pCMC66 only in the desired inverted orientation. By inversion in this sense it is meant that the normal reading direction of the TMV fragment is oppositely oriented with the normal transcription direction of both the promoter and the polyadenylation sequence of the host vector. The plasmid pCMC1054 is an intermediate transcription and expression plasmid constructed to enable transcription of a negative RNA strand complementary to the target RNA transcript encoded by the coat protein coding region of the TMV genome. In addition, the negative RNA strand transcript encoded by this vector also contains a region complementary to a substantial portion of the 3' non-coding region of the TMV genome.

In order to prepare the intermediate expression vector, pCMC1054, for transfer into a plant genome, the plasmid was digested with restriction enzyme Sa1 I and a transfer vector pCMC92 was also digested with Sa1 I. The transfer vector pCMC92 contains the T-DNA border regions from the Ti-plasmid of *A. tumefaciens* and also contains a kanamycin resistance coding gene (APH 3' II).which functions in plants and plant cells to allow selection for kanamycin resistance of plant cells which have stably taken up and are expressing the transforming DNA. The T-DNA border regions are indicated by the arrowhead symbols and the designations RB (right-border) and LB (left-border) in FIGS. 3–5. The plasmid pCMC92 also includes a series of restriction sites (SstI, SmaI/XmaI, BamHI, XbaI, SalI) upstream of the APH 3' II gene. The APH 3' II gene in pCMC92 includes an appropriate promoter (nopaline synthase) and termination sequence (also nopaline synthase). The two fragments are ligated together to form a plant expression vector, designated pCMC1060, illustrated at the bottom of FIG. 3. The expression vector, pCMC1060, contains the antibiotic resistance gene (APH 3' II) together with an expression cassette consisting of the nopaline synthesase (Nos) promoter and polyadenylation sequence, oriented in reversed orientation to the TMV sequence including the coat protein coding region. In addition, of course, the vector contains the *A. tumefaciens* border regions of the T-DNA of the Ti plasmid.

After confirmation of the structure of pCMC1060, *E. coli* containing the plasmid were conjugated with *A tumefaciens* strain LBA4404 and preferential selection was made for *A. tumefaciens* conjugants which contained the pCMC1060 plasmid therein. The resulting *A. tumefaciens* strain was used to transform tobacco tissue of variety Havana 425 by stem inoculation techniques known in the art. Transformed tobacco cells from the stem inoculation were selected in tissue culture for resistance to kanamycin. The resulting cultures were subsequently assayed and shown to express the gene expressed by the antibiotic resistance marker (aminoglycoside 3' phosphotransferase II). The cultures were successfully assayed for said transformation marker protein, and callus cultures of these transformed cells were then regenerated using standard techniques into whole intact plants.

Ten of the regenerated tobacco plants produced from the transformation with pCMC1060 refered to above were then challenged with tobacco mosaic virus. The plants were inoculated with common strain TMV through a standard protocol. The virus was mixed in an aqueous solution in a buffer. Fine corundum was then mixed in with the virus as an abrasive. A gauze pad was then dipped in the abrasive/virus mixture and rubbed on half a leaf of the tobacco plant. The density of the virus content in the buffer solution was adjusted experimentally until it was at a level which would produce approximately 100 lesions per leave in a control non-transformed Hewana 425 tobacco plant. This density corresponded approximately to an optical density. Several leaves on each plant were inoculated. Havanna tobacco plants are normally local lesion hosts for TMV, meaning that infection leads to small localized lesions. It was therefore the intent to inoculate the plants with TMV and ascertain from the gross number and size of lesions a measure of the quantitative effectiveness of the plant's resistance to TMV. Of the twenty-four regenerated transformed plants so exposed, most exhibited a lesion number comparable to that contained in the control plants, i.e. on the order of 100 per leaf. It would be expected that the transformed plants would vary highly in their effectiveness of expression of the chimeric gene due to the random nature of the insertion of the chimeric gene into the plant genome. Eight plants exhibited unusual response to the inoculation procedure indicating a level of quantifiable resistance to infection by the virus. These eight plants had lesion counts that averaged one-tenth as high (i.e on the order of 10) as the control plants. This is an indication that these eight regenerates exhibited a measure of resistance to TMV. These regenerates are currently being reproduced to verify that the trait is fully inheritable.

Alternative Negative Strand RNA for TMV

A similar process was also followed for the Pst I fragment of pOM5H2. The plasmid pOM5H2 was digested with Pst I and the smaller of the resulting fragments was ligated into the expression plasmid pCMC66, which also had been previously digested with Pst I. Two plasmids were obtained by this process, which differed only in the direction of their orientation of the TMV fragment with relation to the host portion of pCMC66. The two plasmids were designated pCMC1052 and pCMC1053. Restriction mapping was done on both plasmids which demonstrated that pCMC1052 carried the TMV fragment in an inverted orientation with respect to the nopaline synthase promoter region and polyadenylation sequence. In other words, it was again intended that the promoter be oppositely oriented relative to the normal reading direction of the gene so that transcription of the gene would yield a negative-strand RNA complementary to the natural viral RNA strand.

Once pCMC1052 was obtained, the resulting plasmid manipulations were identical to those described above with pCMC1050, with pCMC1052 and its progeny being substituted for pCMC1050 and its progeny. The resulting transformed plants have been regenerated and will be analyzed in a similar fashion as described above with the plants transformed with pCMC1060.

EXAMPLE 2

Inhibition of Endogenous Gene Expression Nopaline Synthase

In demonstrating the ability to inhibit expression of an endogenous gene, tobacco plants were selected carrying an endogenous gene for nopaline synthase (Nos). This gene is not normally present in tobacco plants, but has been introduced, through genetic manipulation, into a line of somatically normal, fertile, stable tobacco plants which transmit the intact nopaline synthase gene to their progeny through normal genetic inheritance (Barton et al., Cell 32: 1033–1043 (1983)). Thus, for the purposes of demonstrating this principle, this gene and its expression can be considered endogenous in this plant line. To demonstrate inhibition of the phenotypic expression of this model endogenous gene, a chimeric gene was constructed which directs the synthesis of a negative RNA strand complementary to a large portion of the middle region of the nopaline synthase messenger RNA (mRNA). The fragment chosen was 824 base pairs long. This chimeric gene was constructed and introduced into the genome of cells from this plant line, referred to as HADH plants.

Construction of the chimeric gene and the transfer plasmid to transform plant cells with that gene is diagrammed in FIG. 5. A fragment of the nopaline synthase gene was prepared from a plasmid, pCMC1, by double digestion with C1a I and Sph I. The fragment is separated from the other gene fragments by electrophoresis and ligated with plasmid pUC18, which had previously been digested with Acc I and Sph I. The result of this ligation, designated pUCNos, contained the nopaline synthase fragment flanked by several useful and plasmid unique restriction sites. The fragment of the nopaline synthase gene included within the plasmid represented more than half the total length of the nopaline synthase gene.

The plasmid pUCNos was then digested with Hind III and Sma I to yield two fragments, the smaller of which was selected. That fragment was ligated in an orientation specific manner to expression vector pCMC60, which had been previously digested with Hind III and Sma I, to yield an intermediate expression cassette for a negative RNA strand complementary to the Nos mRNA, designated pCMC6ONos.

To prepare the vector for transforming plant cells, plasmid pCMC6ONos was digested with Xho I. The resulting fragment was ligated into two vectors, pCMC91 and pCMC92, both of which have been previously digested with Sal I. Because there are two directions in which the Nos gene could be inserted into each of the two vectors, there were four transfer vectors created, and these were designated 91NosRA, 91NosRB, 92NosRA and 92NosRB, where 91 and 92 refer to the transfer vector employed in the construction. The A and B notation refers to the two possible orientations of the Nos negative RNA strand produced by the expression cassette relative to the orientation of the dominant selectible marker (kanamycin resistance gene—APH 3' II).

Tobacco stems of variety HADH were inoculated and transformants selected for kanamycin resistance, as described with reference to Example 1 above. Transformant cultures were produced and identified which had putatively been transformed by the chimeric gene coding for the negative RNA stand for the Nos gene. These cultures were all assayed for nopaline production and were found to produce no nopaline.

The following plasmids have been deposited the American Type Culture Collection, Rockville, Md., U.S.A. (ATCC) under the terms of the Budapest Treaty on the International Recognition of the Deposit of Microorganisms for the Purposes of Patent Procedure and Regulations thereunder (Budapest Treaty) and thus are maintained and made available according to the terms of the Budapest Treaty. Availability of such strains is not to be construed as a license to practice the invention and contravention of the rights granted under the authorities of any government in accordance with its patent laws.

The deposit of plasmids have been assigned the indicated ATCC deposit numbers. The plasmids have also been deposited with the Master Culture Collection (CMCC) of Cetus Corporation, Emeryville, Calif., U.S.A., and assigned the following indicated CMCC deposit numbers.

| Plasmid | CMCC Deposit No. | ATCC Deposit No. |
| --- | --- | --- |
| pCMCl in *E. Coli* MM294 | 1985 | 39641 |
| pCMC92 in *E. Coli* | 2306 | 53093 |
| pCMC91 in *E. Coli* | 2307 | 53094 |
| pCMC1060 in *E. Coli* | 2401 | 53243 |
| pCMC1061 in *E. Coli* | 2400 | 53242 |

Figure 4:
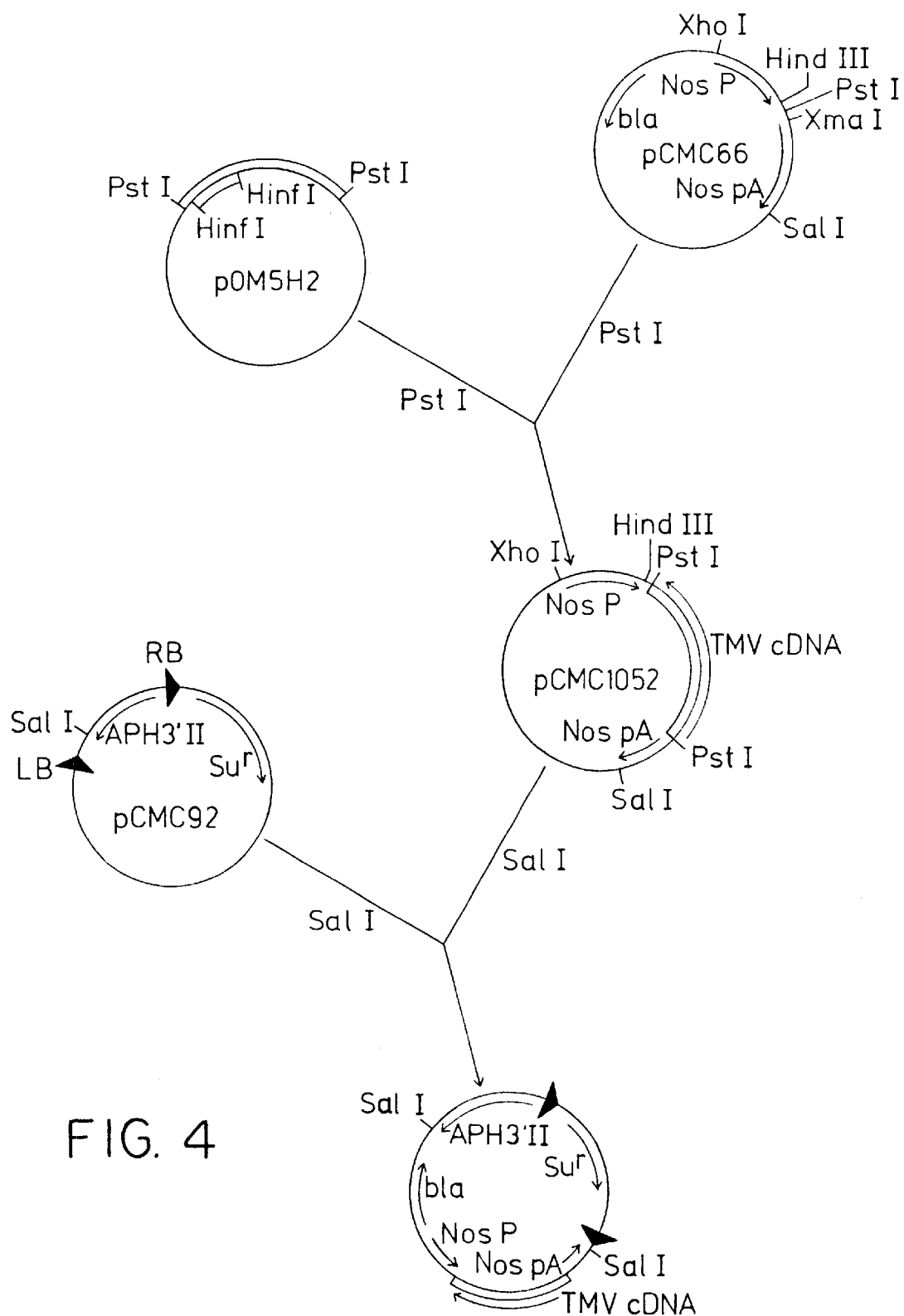
FIG. 4 is a schematic diagram showing the plasmid manipulations according to an alternate method detailed in Example 1 below.
Figure 5:
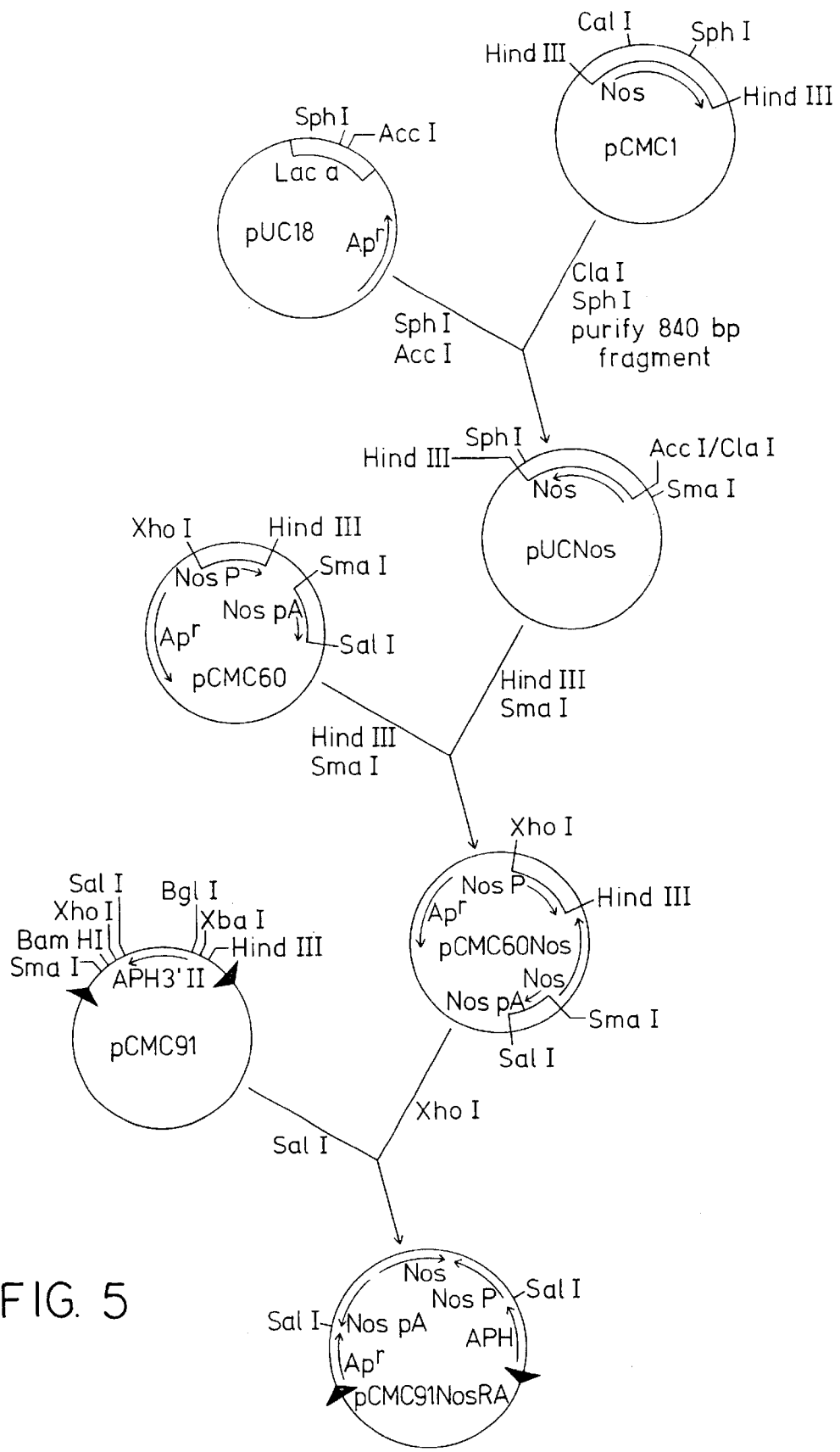
FIG. 5 is a schematic diagram showing the plasmid manipulations detailed in Example 2 below.

The deposited plasmids listed above, pCMC1060 and pCMC1061, not only are ilustrative of the embodiment of this invention used by the inventors here, but are also adaptable for use as vectors for practice of the method disclosed here for other target RNA strands. For example, and most simply, plasmid pCMC1061 can be digested with Sa1 I to yield two smaller plasmids, pCMC1052 and pCMC92, reversing the last step in FIG. 4. The plasmid pCMC66 can be recovered from pCMC1052 by digestion with Pst I. The two plasmids pCMC66 and pCMC92 can then be used with any DNA sequence coding for a target RNA of interest to construct an expression and transfer plasmid capable of causing the transcription of the desired negative strand RNA in plant cells.

What is claimed is:

1. A method for introducing a trait of virus resistance into a dicotyledenous plant comprising the steps of:

introducing into cells of a dicotyledenous plant by Agrobacterium-mediated transformation a chimeric DNA sequence which causes the transcription in the cells of a negative strand RNA which is sufficiently complementary in nucleotide sequence to a target RNA strand which is an RNA produced by a virus so that the hybridization of the negative strand RNA to the RNA produced by the virus in vivo will inhibit pathogenic activity of the virus;

generating a whole mature plant from said cells; and verifying in said plant the virus resistance trait.

2. A method as claimed in claim 1 wherein the target RNA strand is the RNA of tobacco mosaic virus.

3. A virus resistant morphologically normal dicotyledenous plant comprising:

cells which have in their genome a chimeric DNA sequence which causes the transcription in the cells of a negative strand RNA sufficiently complementary to a target viral RNA strand so that the negative RNA strand will specifically associate with the target viral RNA strand to inhibit target RNA strand activity in vivo in the cells of the plant, the target viral RNA strand being selected from the group consisting of a portion of the RNA of a virus and the transcription product created in a plant cell by a virus, the chimeric DNA sequence having been inserted into the parental line of the dicotyledenous plant by Agrobacterium-mediated transformation.

4. A tobacco plant comprising cells which have in their genome a chimeric DNA sequence which causes the transcription in the cells of a negative strand RNA which is sufficiently complementary to a portion of a target RNA strand so as to associate with the target RNA strand in vivo to inhibit target RNA strand activity in the cells, the target RNA strand selected from the group consisting of a RNA product of viral infection of the cell, and a viral RNA itself, the chimeric DNA sequence having been inserted into the parental line of the plant by Agrobacterium-mediated transformation.

5. A tobacco plant as claimed in claim 4 wherein the target RNA strand is the coat protein in RNA of tobacco mosaic virus.

6. A tobacco plant as claimed in claim 5 wherein the target RNA strand is the RNA of tobacco mosaic virus.

7. Seeds of a plant as claimed in claim 3.

8. Seeds of a tobacco plant as claimed in claim 4.

9. A virus-resistant dicotyledonous plant comprising in its chromosomal genome a DNA construct comprising a plant-expressible promoter upstream from a DNA sequence which causes the transcription of a negative strand RNA complementary to viral RNA.

10. A virus-resistant plant comprising in its genome a DNA construct comprising a plant-expressible promoter upstream from a DNA sequence which causes the transcription of a negative strand RNA complementary to viral RNA, the DNA sequence introduced into a parent of the plant through Agrobacterium-mediated plant transformation.

11. A virus-resistant plant comprising in its genome a DNA construct comprising a promoter normally operable in plant cells upstream from a DNA sequence which causes the transcription of a negative strand RNA which is complementary to viral RNA and which inhibits pathogenesis by the virus.

12. A virus-resistant dicotyledonous plant comprising in its genome a DNA construct comprising a promoter normally operable in plant cells upstream from a DNA sequence which causes the transcription of a negative strand RNA which is complementary to viral RNA and which inhibits pathogenesis by the virus.

13. A virus-resistant plant comprising in its genome a DNA construct comprising a promoter normally operable in plant cells upstream from a DNA sequence which causes the transcription of a negative strand RNA which is complementary to viral RNA and which inhibits pathogenesis by the virus, wherein the DNA construct was introduced into a parent of the plant by Agrobacterium-mediated plant transformation.

14. A method for producing a virus-resistant dicotyledonous plant comprising the steps of:

(a) introducing into the chromosomal genome of a dicotyledonous plant cell a recombinant DNA molecule comprising a plant-expressible promoter upstream from a DNA sequence which causes the transcription of a negative strand RNA complementary to viral RNA;

(b) recovering transformed plant cells; and (c) regenerating virus-resistant dicotyledonous plants from said transformed cells.

15. A method for producing a virus-resistant plant comprising the steps of:

(a) introducing into the genome of a plant cell by Agrobacterium-mediated transformation a recombinant DNA molecule comprising a promoter normally operable in plant cells upstream from a DNA sequence which causes the transcription of a negative strand RNA complementary to viral RNA;

(b) recovering transformed plant cells; and (c) regenerating virus-resistant plants from said transformed cells.

16. A method for producing a virus-resistant plant comprising the steps of:
  (a) introducing into the genome of a plant cell a recombinant DNA molecule comprising a promoter normally operable in plant cells upstream from a DNA coding sequence which causes the transcription of a negative strand RNA sufficiently complementary to a viral RNA to inhibit pathogenesis by the virus;
  (b) recovering transformed plant cells; and
  (c) regenerating virus-resistant plants from said transformed cells.

17. A method for producing a virus-resistant dicotyledonous plant comprising the steps of:
  (a) introducing into the genome of a dicotyledonous plant cell a recombinant DNA molecule comprising a promoter normally operable in plant cells upstream from a DNA coding sequence which causes the transcription of a negative strand RNA sufficiently complementary to a viral RNA to inhibit pathogenesis by the virus;
  (b) recovering transformed plant cells; and
  (c) regenerating virus-resistant dicotyledonous plants from said transformed cells.

18. A method for producing a virus-resistant plant comprising the steps of:
  (a) introducing into the genome of a plant cell by Agrobacterium-mediated transformation a recombinant DNA molecule comprising a promoter normally operable in plant cells upstream from a DNA coding sequence which causes the transcription of a negative strand RNA sufficiently complementary to a viral RNA to inhibit pathogenesis by the virus;
  (b) recovering transformed plant cells; and
  (c) regenerating virus-resistant plants from said transformed cells.

19. A chimeric DNA sequence comprising a promoter normally operable in plant cells and a DNA sequence coding for the transcription of a negative strand RNA which is sufficiently complementary in nucleotide sequence to a target RNA strand produced by a virus so that expression of the chimeric DNA sequence in plant cells will inhibit pathogenic activity of the virus.

20. A plant cell comprising in its genome the chimeric DNA sequence of claim 19.

21. A DNA construct comprising a plant-expressible promoter upstream from a DNA sequence which causes the transcription of a negative strand RNA complementary to viral RNA, wherein the promoter is capable of causing transcription of said DNA sequence in a plant call.

22. A virus-resistant dicotyledonous plant cell comprising the DNA construct of claim 21.

* * * * *